United States Patent
Chen et al.

(10) Patent No.: US 9,211,608 B2
(45) Date of Patent: Dec. 15, 2015

(54) LASER WELDING OF DISC TO CLOSE NEEDLE END

(75) Inventors: David E-bin Chen, Fremont, CA (US); Jeffrey Wayne Etter, Hayward, CA (US)

(73) Assignee: MEDICAL INSTRUMENT DEVELOPMENT LABORATORIES, INC., San Leandro, CA (US)

(*) Notice: Subject to any disclaimer, the term of this patent is extended or adjusted under 35 U.S.C. 154(b) by 899 days.

(21) Appl. No.: 13/419,655

(22) Filed: Mar. 14, 2012

(65) Prior Publication Data

US 2012/0239071 A1    Sep. 20, 2012

Related U.S. Application Data

(60) Provisional application No. 61/452,898, filed on Mar. 15, 2011.

(51) Int. Cl.
| | |
|---|---|
| *A61B 17/32* | (2006.01) |
| *B23K 26/24* | (2014.01) |
| *B23K 26/22* | (2006.01) |
| *B23K 26/28* | (2014.01) |
| *B23K 26/38* | (2014.01) |
| *A61F 9/007* | (2006.01) |

(52) U.S. Cl.
CPC ........... *B23K 26/243* (2013.01); *A61F 9/00763* (2013.01); *B23K 26/22* (2013.01); *B23K 26/28* (2013.01); *B23K 26/38* (2013.01)

(58) Field of Classification Search
CPC . A61F 9/00736; A61F 9/00763; B23K 26/22; B23K 26/243; B23K 26/28; B23K 26/38

USPC ......................................... 606/167–171, 185
See application file for complete search history.

(56) References Cited

U.S. PATENT DOCUMENTS

| | | | |
|---|---|---|---|
| 3,279,640 A | 10/1966 | Dodson | |
| 4,696,298 A * | 9/1987 | Higgins et al. | ................ 606/171 |
| 4,697,058 A | 9/1987 | Mueller | |
| 5,269,765 A | 12/1993 | Kuracina | |
| 5,630,827 A | 5/1997 | Vijfvinkel | |

(Continued)

FOREIGN PATENT DOCUMENTS

| | | |
|---|---|---|
| EP | 1997461 | 12/2008 |
| WO | 2008/033874 | 3/2008 |

OTHER PUBLICATIONS

International Search Report and Written Opinion for Application No. PCT/US2012/028992 dated Jul. 16, 2012 (9 pages).

*Primary Examiner* — Katrina Stransky
(74) *Attorney, Agent, or Firm* — Michael Best & Friedrich LLP (57) ABSTRACT

A cutting apparatus has a handle and a hollow needle having a first end connected to the handle and a second end. The needle outer diameter is about 0.04 inch or less. An end cap is formed from a blank material. Preferably, at least one bridge is formed between the end cap and the blank material. The end cap is welded to the second end to enclose the needle and then the bridge is cut. The end cap has substantially flat inner and outer surfaces. The needle has a port and a hollow cutter that slides within the needle. The cutter has a first end connected to a drive, and a second end having a cutting edge. An outer cutter diameter is less than the needle inner diameter. The drive reciprocates the cutter within the needle to perform a cut.

20 Claims, 5 Drawing Sheets

(56) References Cited

U.S. PATENT DOCUMENTS

| | | |
|---|---|---|
| 5,733,297 A | 3/1998 | Wang |
| 5,807,401 A * | 9/1998 | Grieshaber et al. ........... 606/107 |
| 6,001,083 A | 12/1999 | Wilner |
| 7,326,065 B2 | 2/2008 | Frutschy et al. |
| 7,785,110 B2 | 8/2010 | Li |
| 7,897,891 B2 | 3/2011 | Chen et al. |
| 2002/0052617 A1 | 5/2002 | Anis et al. |
| 2007/0093793 A1 * | 4/2007 | Maurer et al. .................... 606/4 |
| 2008/0183199 A1 | 7/2008 | Attinger |
| 2009/0082715 A1 | 3/2009 | Charles |
| 2009/0157111 A1 * | 6/2009 | Goh et al. ..................... 606/171 |
| 2010/0222749 A1 | 9/2010 | Baid |

\* cited by examiner

LASER WELDING OF DISC TO CLOSE NEEDLE END

FIELD

Embodiments of the invention relate to the needle end of ophthalmic surgical cutting devices and techniques for forming such ends.

BACKGROUND

An ophthalmic cutting device is a surgical instrument for use in eye surgery. A guillotine-style ophthalmic cutting device may be used to remove portions of the vitreous humor of the eye. A guillotine-style ophthalmic cutting device includes two principal parts: (1) a hollow needle including a cutting port and (2) a slidable, cutter positioned inside the needle. The cutter may also be hollow. In use, the ophthalmic cutting device is inserted into an incision in the eye. As vitreous tissue enters the port of the needle, the cutter slides past the port to cut the tissue. A vacuum may be applied to the cutter to remove the cut tissue from the cutting device.

SUMMARY

One disadvantage of current ophthalmic cutting devices is that excessive distance between the tip of the cutting device and the port limits how close to the retina the tool can be used. Thus, one object of certain embodiments of the invention is to provide an ophthalmic cutting device with a reduced distance between the tip and the port. Another disadvantage of current ophthalmic cutting devices is that the thickness of the end cap of the needle or material inside the cutting device, for example weld flux, limits the distance that the interior cutter can travel. Thus, another object of certain embodiments of the invention is to provide an ophthalmic cutting device with a thinner end or reduced material inside the cutting device to increase the travel distance for the interior cutter.

In one particular embodiment, the invention is directed to an ophthalmic surgical cutting apparatus. The device includes a handle and a hollow needle. The needle has a first end connected to the handle and a second end opposite the first end. The needle also has an inner surface defining an inner diameter and an outer surface defining an outer diameter. The outer diameter is about 0.036 inch or less. An end cap shaped and sized as a plate is formed from a blank material such that at least one bridge is left between the end cap and the blank material after the end cap is formed. The end cap is welded to the second end by a weld to enclose the needle. The bridge is cut when the end cap is welded to the second needle end. The end cap has a substantially flat inner surface and a substantially flat outer surface. The needle additionally has a port positioned a predetermined or "tip" distance from the outer surface of the end cap.

The device also includes a hollow cutter that is slidably disposed within the needle. The cutter has a first end connected to a drive and a second end opposite the first end. The cutter also has a cutting edge disposed at the second end of the cutter. An outer cutter surface defines an outer cutter diameter that is less than the inner diameter of the needle. The drive reciprocally moves the cutter within the needle to alternately cover and uncover the port with the second cutter end to perform a cutting operation. The cutter also travels an over-travel distance past the port.

Another aspect of the invention is a method of welding an end cap onto an end of a hollow needle of an opthalmic surgical cutter. The method includes forming an end cap from a blank material, leaving at least one bridge coupling the end cap to the blank material, forming a port through the side of the needle, welding the end cap to the needle to enclose one end of the needle, and cutting the at least one bridge during welding.

These and other aspects of the invention, together with the organization and operation thereof, will become apparent from the following detailed description when taken in conjunction with the accompanying drawings.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

With reference to FIGS. 1 through 4 there is shown a guillotine-style ophthalmic cutting device 20 for use in ophthalmic surgery. The device 20 includes a handle 22 and a circular cylindrical hollow needle 24. The needle 24 is typically size 20 gauge or smaller, and includes a first end 26 connected to the handle 22 and a second end 28 opposite the first end 26. The needle 24 also includes an inner surface 32 that defines an interior region 34 and an inner diameter 36. An outer surface 38 of the needle 24 defines an outer diameter 42. The outer diameter 42 can range from about 0.012 inch to about 0.04 inch but is typically about 0.036 inch. The inner surface 32 and the outer surface 38 define a wall thickness 44. The wall thickness 44 can range from about 0.001 inch to about 0.005 inch. The second end 28 of the needle 24 includes an end surface 46. An end cap 48 is fused to the end surface 46 by a weld 52 to enclose the needle 24. The end cap 48 is a circular disc that includes a substantially flat inner surface 54, a substantially flat outer surface 56, and a circumferential surface 58 disposed between the inner surface 54 and the outer surface 56. The inner surface 54 and the outer surface 56 define an end cap thickness 62. The end cap thickness 62 is typically less than or equal to about 0.005 inch.

Figure 1:
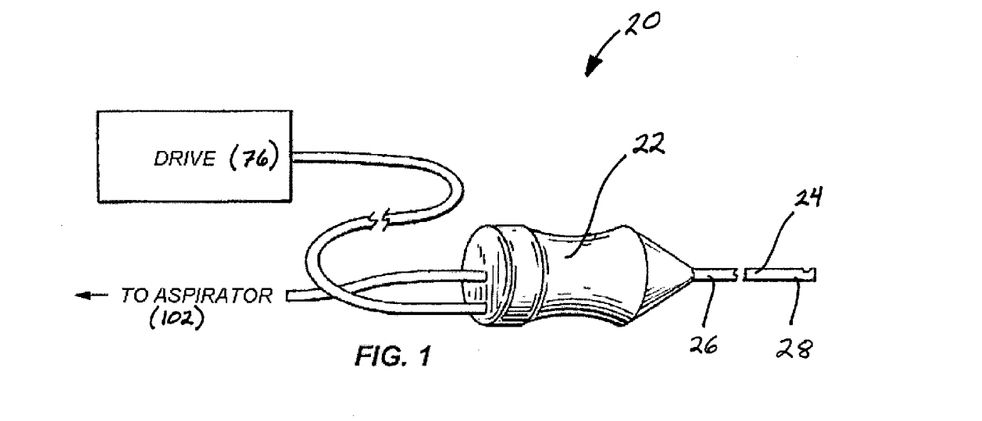
FIG. 1 is a perspective view of an exemplary ophthalmic surgical cutting apparatus embodying aspects of the invention.
Figure 2:
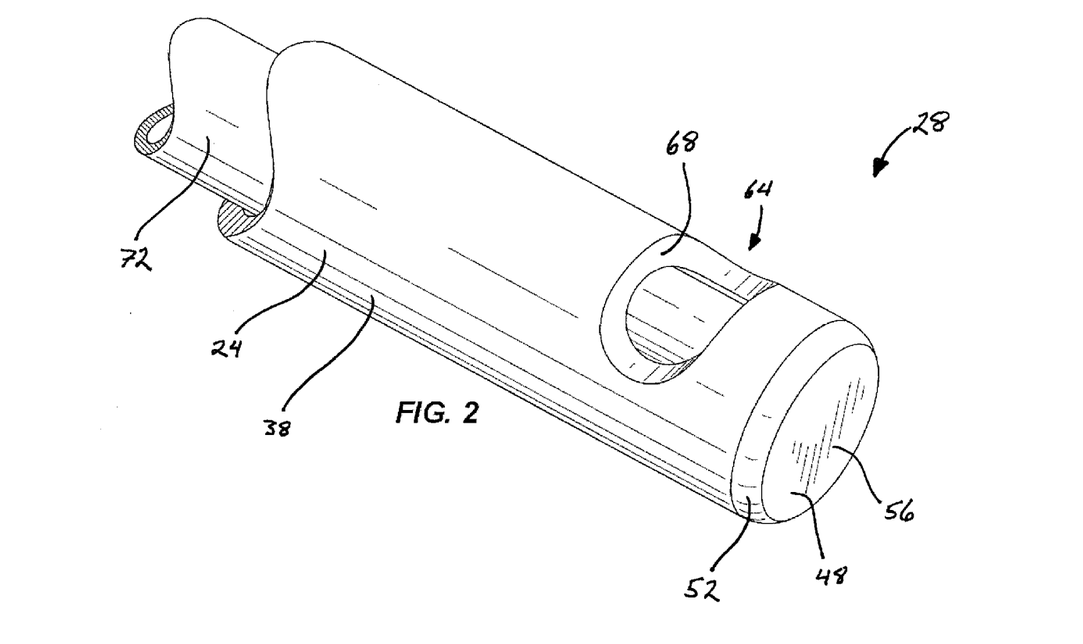
FIG. 2 is an enlarged, perspective view of a portion of the device of FIG. 1
Figure 3:
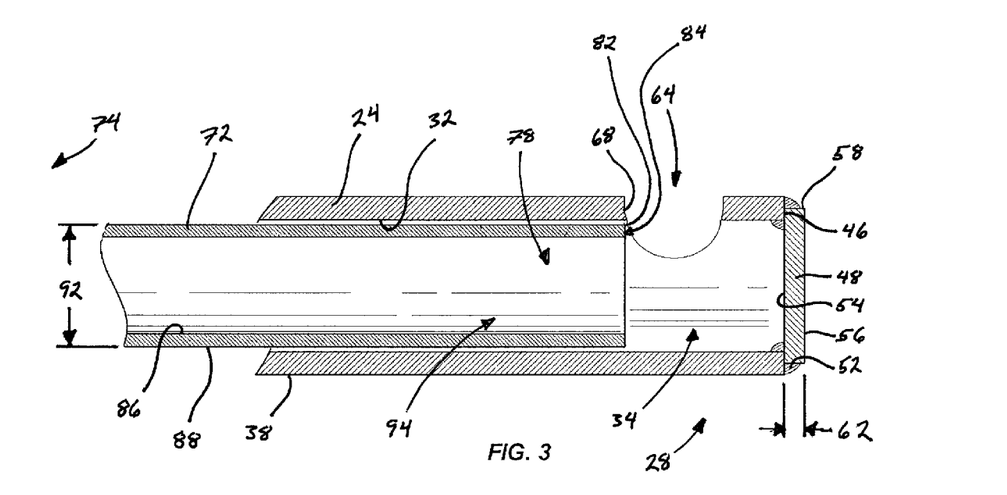
FIG. 3 is a sectional side view of the device of FIG. 1.
Figure 4:
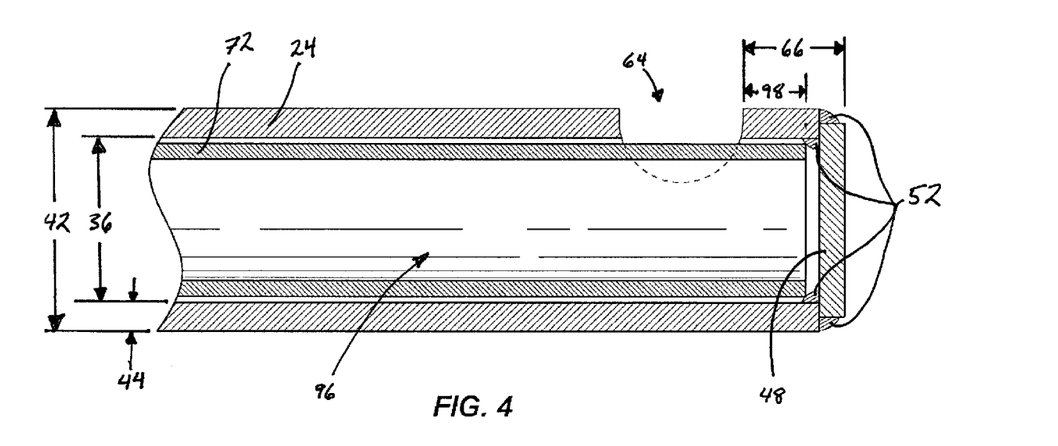
FIG. 4 is a sectional side view of the device of FIG. 1.

As should be apparent from the description above, the needle 24 of the cutting device is relatively small. The magnitude of the values provided above falls, in general, in the hundreds of microns. Thus, the drawings, and particularly, FIG. 2, are not to scale. The drawings illustrate enlarged versions of the actual components. Because the components are so small, they can not, in general, be handled using ordinary techniques or equipment. For example, a welding machine and techniques used in automotive repair is completely unsuitable when attempting to form a tip or end on the needle 24. The weld 52 and techniques for forming it are described in greater detail below.

A port 64 is positioned near the end cap 48 and extends through the needle 24 from the inner surface 32 to the outer surface 38. The port 64 is positioned a tip distance 66 from the outer surface 56 of the end cap 48. The port 64 includes a port surface 68. In the illustrated embodiments, the end surface 46 and the port surface 68 are substantially flat.

A circular cylindrical hollow cutter 72 is slidably positioned within the needle 24. The cutter 72 includes a first cutter end 74 connected to a drive 76, and a second cutter end 78 opposite the first end 74. The second end 78 includes a cutting edge 82 and a cutting surface 84. In the illustrated embodiments, the cutting surface 84 is substantially flat. The cutter 72 also includes an inner cutter surface 86 and an outer cutter surface 88. The outer surface 88 defines an outer cutter diameter 92 that is less than the inner diameter 36 of the needle 24. The drive 76 is configured to selectively linearly reciprocate the cutter 72 within the needle 24 between a first position 94 (shown in FIG. 3), and a second position 96 (shown in FIG. 4). In the first position 94, the cutter 72 is located away from the end cap 48 sufficiently to at least partially uncover the port 64. In the second position 96, the cutter 72 is located near the end cap 48 to cover the port 64, and has moved an additional or overtravel distance 98 beyond the port 64.

In use, the needle of the device 20 is inserted into an incision in an eye of a patient to cut and remove vitreous tissue from the eye. The drive 76 is activated by a user (e.g., a surgeon). Using the handle 22, the port 64 of the needle 24 is directed against vitreous of the eye. The drive 76 reciprocates the cutter 72 across the port 64 between the first position 94 and the second position 96. When the cutter 72 is in the first position 94, the port 64 is open or unobstructed and a portion of the vitreous enters the port 64. When the cutter 72 moves past the port 64 to the second position 96, vitreous is cut by the cutting edge 82 acting in cooperation with the port surface 68. An aspirator 102 is fluidly coupled to the cutter 72. The aspirator 102 creates a suction to remove the cut pieces of vitreous from the device 20 through the cutter 72. The suction created by the aspirator 102 also helps pull vitreous into the port 64 prior to cutting.

Figure 5:
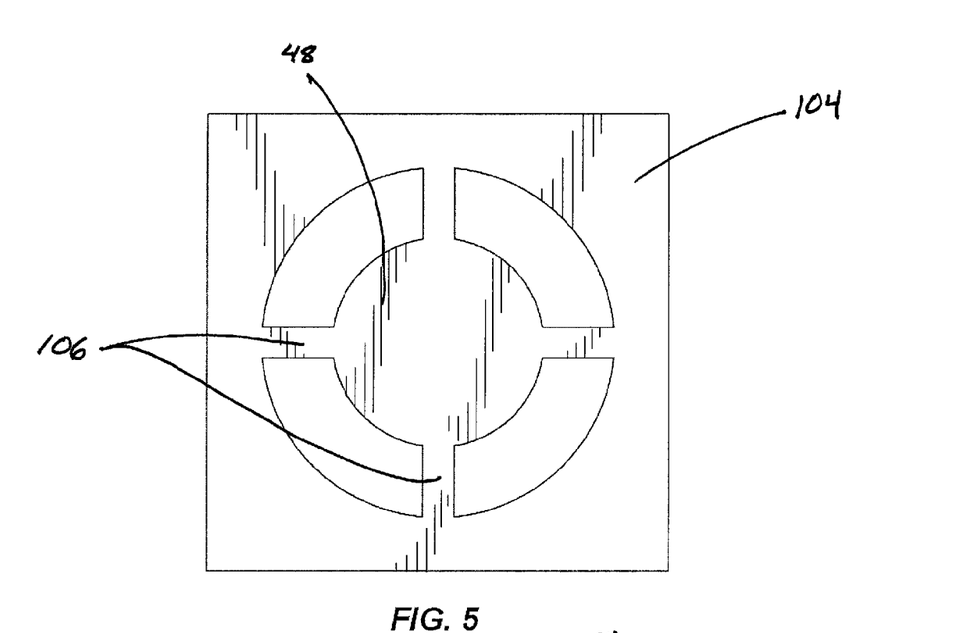
FIG. 5 is a top view of another embodiment of the invention.
Figure 6:
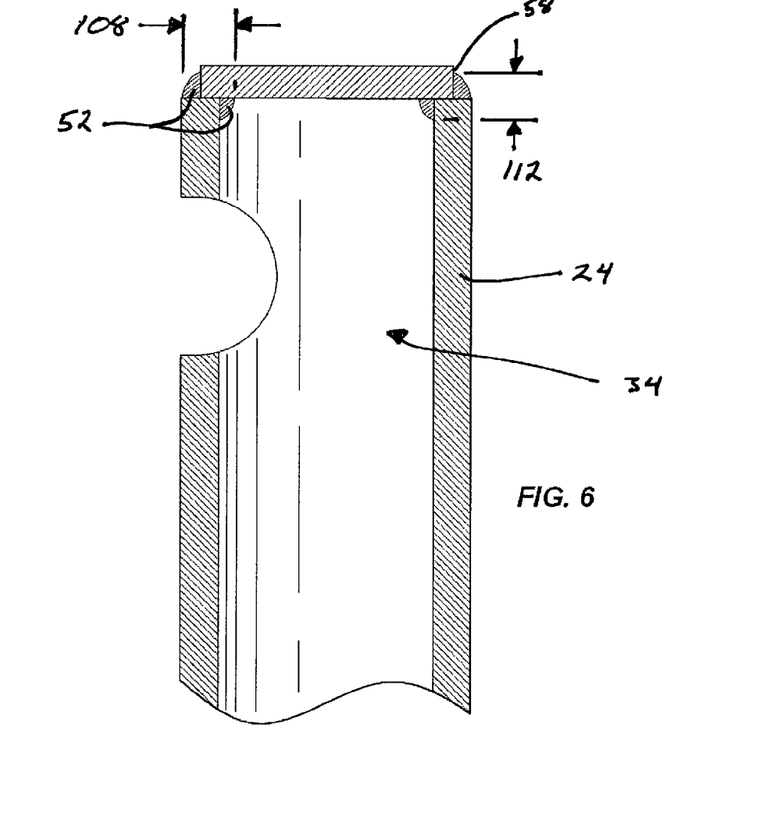
FIG. 6 is a sectional side view of the device of FIG. 1.
Figure 7:
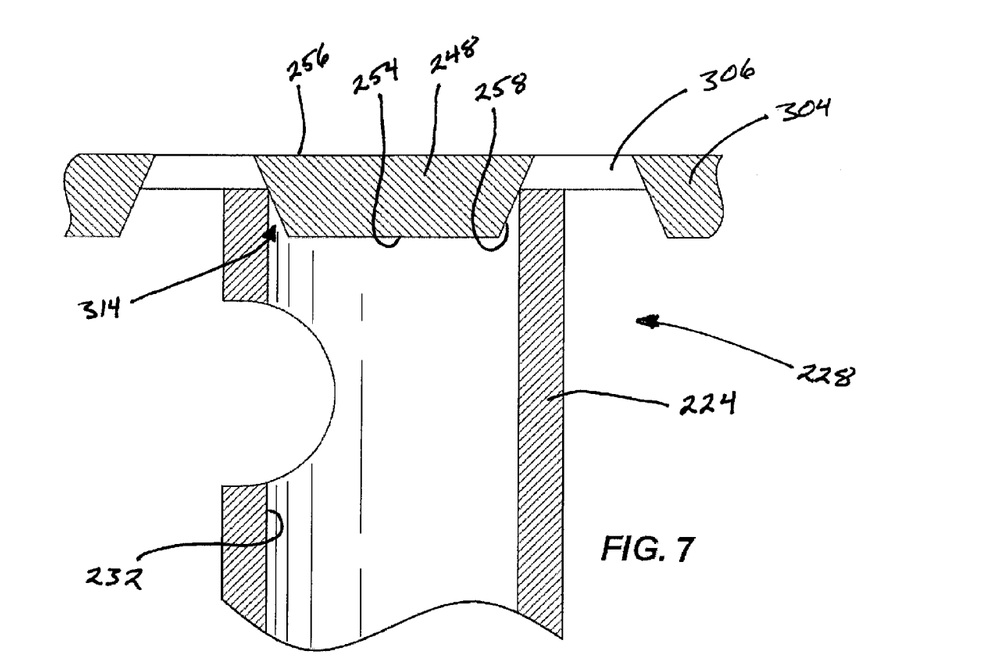
FIG. 7 is a sectional side view of another embodiment of the invention.
Figure 8:
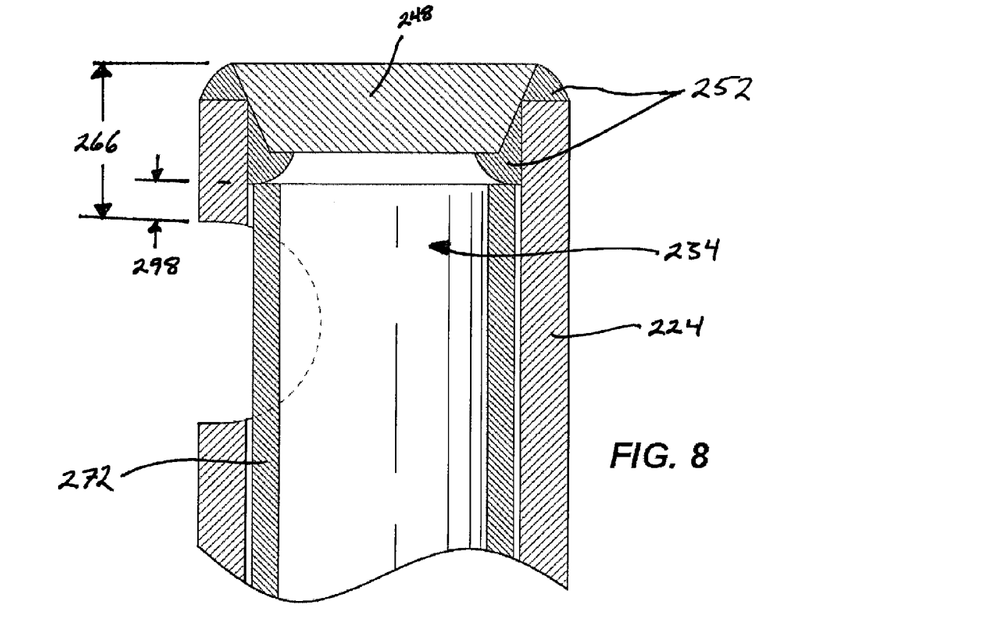
FIG. 8 is a sectional side view of the device of FIG. 5.
Figure 10:
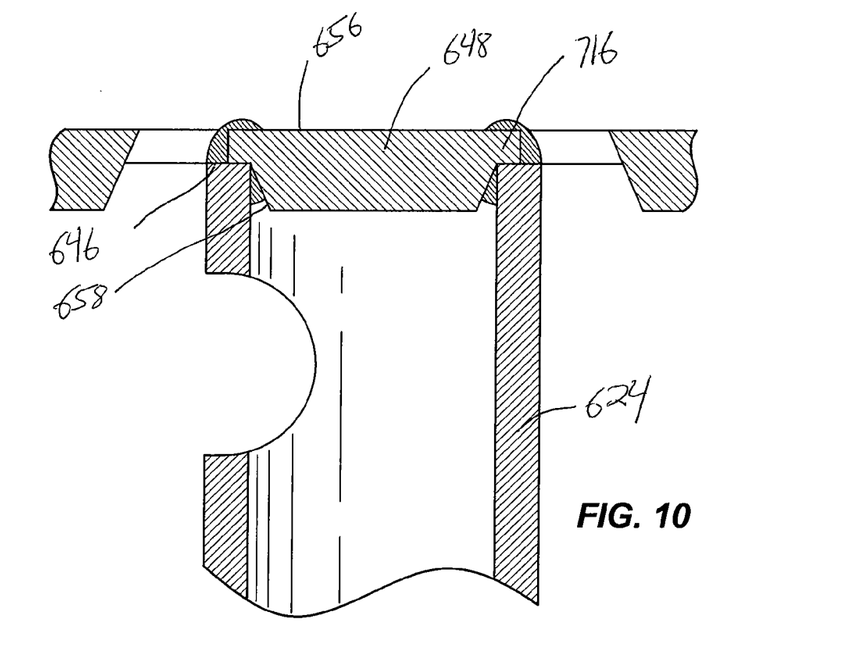
FIG. 10 is a sectional side view of another embodiment of the invention.

With reference to FIG. 5, in one embodiment, the end cap 48 is formed or cut from a blank material 104 by etching, particularly multi-layer chemical etching. In alternative embodiments, the end cap 48 is formed by stamping, casting, laser cutting, machining, or the like. To ensure creation of a proper weld 52, the end cap 48 must be held in contact with the needle 24 during welding. At least three different methods of holding the end cap 48 in place are envisioned. The end cap 48 may be held in place using clamps or by drawing a vacuum on the needle 24. Alternatively, and as shown in FIGS. 7, 8, and 10, the end cap 48 may be held in place by leaving one or more bridges 106 extending between the end cap 48 and the end cap blank material 104 in order to temporarily maintain the end cap 48 connected to the blank material 104. The blank material 104 can then be used to manipulate the end caps 48 into position on the needle 24 for welding. If multiple bridges 106 are used, they provide the additional benefit of preventing the end cap 48 from warping during welding, thereby maintaining the end cap 48 in contact with the needle 24 during welding. Multiple end caps 48 may be formed from a single sheet of blank material 104 simultaneously. If the bridges 106 are left between the end caps 48 and the blank material 104, multiple end caps 48 can simultaneously be moved into position for welding on multiple needles 24 by manipulating a single sheet of blank material 104. The bridges 106 are cut by the welder while welding the end cap 48 to the needle 24, therefore additional processes to remove the bridges 106 are not required.

The weld 52 has a weld width 108 and a weld depth 112. In the illustrated embodiment, the weld width 108 and weld depth 112 are both approximately three times the wall thickness 44. The weld 52 is a laser weld that includes a series of spot welds. The spot welds may be connected or semi-connected depending on the strength of weld 52 desired. During welding, the end cap 48 is positioned on the end surface 46 of the needle 24 and a laser beam (generated by a laser) is directed to specific locations around perimeter of the end cap 48. Energy from the laser beam heats the portions of the end cap 48 and needle 24 at these locations and causes the materials of the two components to melt. When the laser beam is turned off (or otherwise redirected away from the location), the materials from the two pieces 48, 24 fuse to form a weld 52 at that location or spot, thus creating a "spot weld." Unlike other types of welding in which a filler material (often in the form of a wire) is melted and placed in the gap between two components or parts to be welded, the laser welding process does not add material to the cutting device 20. The weld 52 is formed from portions of the end cap 48 and needle 24.

In order to reduce the collateral damage to the eye during surgery, the device 20 described herein must be relatively small. The device 20 also requires high tolerances including high tolerance welds. Therefore, computed numerically controlled ("CNC") devices are contemplated for accurately manipulating, holding, grinding, and/or welding the components of the device 20. For example, a CNC welder may be used to move the welding source (e.g., the laser) while the work pieces (i.e., the end cap 48 and needle 24) remain stationary. Alternatively, a CNC device may move the needle 24 and end cap 48 relative to a fixed welder to weld the end cap 48 to the needle 24. A CNC device is also contemplated for holding the end cap 48 in position on the needle 24 during welding.

Similar types of welding (i.e., welding that does not require a filler material) may also be used. The alternative techniques include friction welding and electric discharge welding. Regardless of the exact type of welding used, it is desirable to achieve a weld 52 having a width 108 and depth 112 that are approximately three times or less than the wall thickness 44. In some embodiments, the weld 52 may protrude past the end cap 48 (see FIG. 9) or the end cap thickness 62 may be thicker than 0.005 inch. In either case, a secondary grinding operation can be used to remove protruding weld material or reduce the end cap thickness 62. The end cap 48 may alternatively be welded to the inner surface 32 of the needle 24 or the outer surface 38 of the needle 24. In addition, the needle 24, the end cap 48, and the cutter 72 may be of a shape other than a circular cylinder, including a triangular cylinder, a square cylinder, or another shape. In the embodiment shown in FIG. 3, the port 64 is a semi-circle when viewed from the side. In other embodiments, the port 64 may be of another shape, including a triangle, square, or an other shape. The port surface 68 may additionally be beveled, or partially beveled, to improve cutting. The cutting surface 84 of the cutter 72 may also be beveled or have some other shape to improve cutting. In still other embodiments, one or both of the end surface 46 and the port surface 68 may be beveled or have some other shape to improve weld quality or help maintain the end cap 48 on the needle 24 for welding.

FIG. 7 illustrates an embodiment where the end cap 248 is chemically etched to create angled surfaces such as a conical circumferential surface 258. The end cap 248 is a conical-frustum in which the substantially flat inner surface 254 is positioned inside the needle 224 and the substantially flat outer surface 256 is positioned outside the needle 224. The conical circumferential surface 258 of the end cap 248 contacts the second end 228 of the needle 224. By sizing the substantially flat inner surface 254 to fit within the needle 224 and sizing the circumferential surface 258 to contact the needle 224, the end cap 248 is easier to align on the needle 224 during manufacturing. The end cap 248 is shown connected to a blank material 304 by bridges 306. The conical circumferential surface 258 and the inner surface 232 of the needle 224 intersect to form a void 314. In some embodiments, the void 314 is configured to allow a portion of the second cutter end 278 of the cutter 272 to extend into the void 314, thereby increasing the overtravel distance 298 and decreasing the tip distance 266. In other embodiments, the void 314 is filled by melted material from the needle 224 and the end cap 248 during welding.

FIG. 8 shows the embodiment of FIG. 7 after the end cap 248 has been welded in place. The weld 252 has been configured to extend into the interior region 234 a minimal distance so that there is still sufficient overtravel distance 298 while minimizing the tip distance 266.

Figure 9:
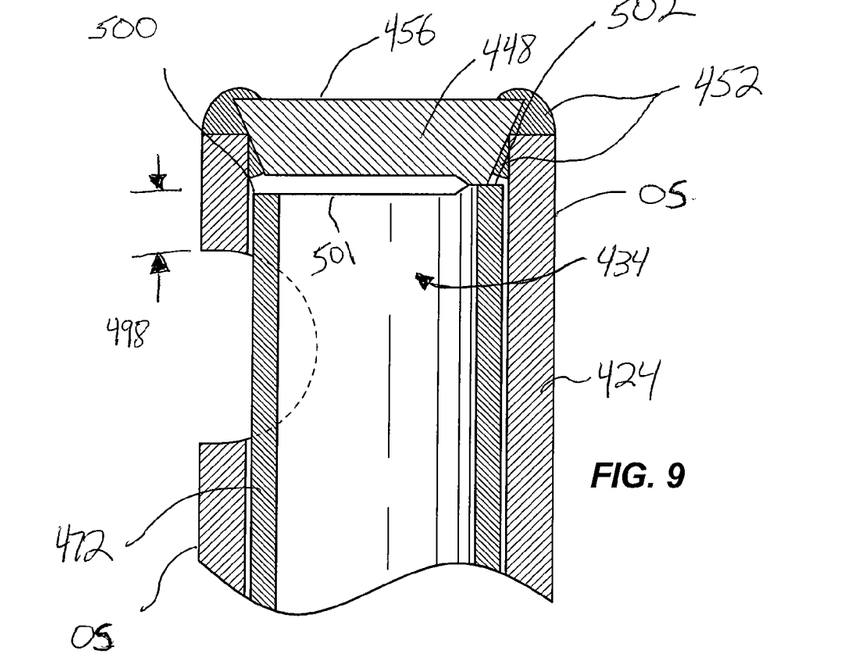
FIG. 9 is a sectional side view of another embodiment of the invention.

FIG. 9 shows an embodiment that is similar to the embodiment shown in FIGS. 7 and 8, but different in that the weld 452 is formed so as to protrude past the end cap 448 instead of extending into the interior region 434. The increased clearance allows a greater overtravel distance 498 in comparison to the embodiment of FIG. 8, but requires a secondary grinding operation to produce the substantially flat outer surface 456 of the cutting device 420. In addition, the weld is formed so as not to extend beyond the outer surface (OS) of the needle 424. During surgical procedures, the needle 424 is often inserted into or through other devices such as a cannula. In ensure proper fit and clearance during such insertions, it is important that the weld not extend beyond the outer surface OS of the needle. As described below with respect to FIG. 10, in some embodiments, the flange is sized so as to provide space for the weld to flow so that molten material does not harden in a manner where the weld extends beyond the outer surface OS.

FIG. 9 also illustrates alternative forms of the end cap and the cutter. The end cap 448 is modified (as compared, for example, to the end cap 72) so that contact between the cutter 472 and end cap 448 is limited to a specific area. In particular, the thickness of the end cap 448 is reduced along most of the cap's width so that a blade portion or cutting edge 500 of the cutter 472 does not contact the end cap 448. Instead only a portion of the cutter (which is not the cutting edge 500) contacts the end cap 448.

An alternative to modifying the end cap 448 (as just described) is to modify the cutter 472. The cutter 472 includes the cutting edge 500, a trailing edge 501, and a leading edge or contact portion 502. The contact portion 502 of the cutter 472 contacts the end cap 448. The alternative configurations of the cutter and end cap can be used alone or in combination with one another. These alternative configurations reduce or prevent contact between the cutting edge 500 and the end cap 448. Such contact tends to dull the cutting edge 500. Eliminating or reducing such contact helps keep the cutting edge 500 sharp.

In some embodiments, and as illustrated in FIG. 10, the end cap 648 is a partial conical-frustum that includes an annular flange 716 disposed about the conical circumferential surface 658 and adjacent to the substantially flat outer surface 656 of the end cap 648. This embodiment has increased surface area contact (as compared to the examples in FIGS. 7 through 9) between the end cap 648 and the end surface 646 of the needle 624. For welding operations that do not add weld material, such as laser welding, the flange 716 beneficially provides more material for forming the weld in comparison to the embodiments of FIGS. 7 through 9. The greater surface area contact and material for welding provide for a stronger weld 52.

The welding operation and techniques described herein can be utilized with a variety of ophthalmic cutting devices. Specifically, the welding operation can be utilized on a cutting device having an inner tube that rotates within an outer tube in response to a first air pressure source positively driving a piston to an open position and a second air pressure source positively driving a piston to a closed position, such as described in U.S. Pat. No. 5,176,628. Another possible cutter which can utilize the welding operation of the present invention is a cutter having an inner tube that reciprocates within an outer tube in response to first and second air pressure sources providing a cyclic pressure differential across a diaphragm, as described in Patent Publication WO2007/092736.

Various features of the invention are set forth in the following claims.

What is claimed is:

1. An ophthalmic surgical cutting apparatus, the apparatus comprising:
  a hollow needle, the needle having
    an inner surface defining an inner diameter,
    an outer surface defining an outer diameter,
    a wall defined between the inner surface and the outer surface and having a wall thickness,
    a first end configured to be connected to a handle,
    a second end opposite the first end,
    an end cap welded to the second end by a weld, the end cap having a substantially flat inner surface, a substantially flat outer surface, and an end cap diameter that is smaller than the outer diameter of the outer surface of the needle, the weld having an inner portion that is positioned within the needle, an outer portion of the weld that is not within the needle, and defining a weld thickness that is greater than the wall thickness, and
    a port positioned a tip distance from the outer surface of the end cap; and
  wherein the hollow needle is configured to receive a hollow cutter having a cutting edge disposed on a distal end and an outer cutter surface defining an outer cutter diameter, the outer cutter diameter of the cutter being less than the inner diameter of the needle, the distal end being movable past the port by an overtravel distance.

2. The ophthalmic surgical cutting apparatus of claim 1, wherein the end cap is laser welded to the second end of the needle from a series of spot welds.

3. The ophthalmic surgical cutting apparatus of claim 1, wherein the end cap is a circular disc.

4. The ophthalmic surgical cutting apparatus of claim 1, wherein the end cap is a substantially conical-frustum shaped disc having a conical circumferential surface, and wherein the substantially flat inner surface is positioned within the needle and the substantially flat outer surface is positioned outside the needle.

5. The ophthalmic surgical cutting apparatus of claim 4, wherein the inner surface of the needle and the circumferential surface form a void.

6. The ophthalmic surgical cutting apparatus of claim 1, wherein the end cap is a substantially conical-frustum shaped disc having a partial conical circumferential surface with an annular flange disposed adjacent the substantially flat outer surface, wherein the substantially flat inner surface is positioned within the needle, the substantially flat outer surface is positioned outside the needle, and a circumferential edge of the second end of the needle is connected to the annular flange.

7. The ophthalmic surgical cutting apparatus of claim 1, wherein the weld has a weld depth, the weld width being substantially the same as the weld depth.

8. The ophthalmic surgical cutting apparatus of claim 1, wherein the weld thickness is three times greater than the wall thickness.

9. The ophthalmic surgical cutting apparatus of claim 1, wherein the cutter is slidably disposed within the needle, the cutter having a first end opposite the distal end, the first end being connected to a drive that reciprocally moves the cutter within the needle to perform a cutting operation.

10. A method of manufacturing an ophthalmic surgical cutting apparatus, the ophthalmic surgical cutting apparatus including an end cap coupled to an end of a hollow needle, the method comprising:
   forming an end cap from a blank material, wherein the forming leaves at least one bridge configured to couple the end cap to the blank material;
   forming a port through the side of the needle, the port being positioned a tip distance from an inner surface of the end cap;
   welding the end cap to the needle to enclose one end of the needle; and
   cutting the at least one bridge during welding.

11. The method of claim 10, further comprising placing a hollow cutter within the needle, connecting the needle to a handle, and connecting the cutter to a drive configured to reciprocate the cutter relative to the needle.

12. The method of claim 10, wherein welding the end cap to the needle includes laser welding the end cap to the needle with a series of spot welds.

13. The method of claim 10, further comprising forming the end cap into a conical-frustum shape and positioning a first end of the conical-frustum end cap inside the needle and positioning a second end of the conical-frustum end cap outside the needle.

14. The method of claim 10, further comprising forming the end cap into a substantially conical-frustum shape with an annular flange disposed adjacent a substantially flat outer surface of the end cap, positioning a substantially flat inner surface of the end cap inside the needle, positioning the substantially flat outer surface of the conical-frustum end cap outside the needle, and welding the annular flange to the needle.

15. The method of claim 10, further comprising forming the end cap by etching through the blank material.

16. The method of claim 10, further comprising forming the end cap by stamping the blank material.

17. The method of claim 10, further comprising forming the end cap by laser cutting the blank material.

18. The method of claim 10, further comprising forming the end cap by casting the blank material.

19. The method of claim 10, further comprising maintaining the end cap on the needle during welding by manipulating the blank material.

20. The method of claim 10, further comprising using a computed numerically controlled device to weld the end cap to the needle.

* * * * *